United States Patent [19]
Fujimoto et al.

[11] Patent Number: 5,036,820
[45] Date of Patent: Aug. 6, 1991

[54] METHOD OF DETERMINING ACTIVATION OF AN EXHAUST GAS CONCENTRATION SENSOR EQUIPPED WITH A HEATER

[75] Inventors: Sachito Fujimoto; Toshihiro Mibe; Takeshi Fukuzawa, all of Wako, Japan

[73] Assignee: Honda Giken Kogyo K.K., Tokyo, Japan

[21] Appl. No.: 579,304

[22] Filed: Sep. 7, 1990

[30] Foreign Application Priority Data

Sep. 12, 1989 [JP] Japan ................................. 1-236099

[51] Int. Cl.$^5$ ............................................ F02D 41/14
[52] U.S. Cl. .................................................. 123/489
[58] Field of Search ....................... 123/440, 489, 589; 204/426

[56] References Cited
U.S. PATENT DOCUMENTS

| | | | |
|---|---|---|---|
| 4,434,764 | 3/1984 | Hasegawa et al. | 123/489 |
| 4,528,957 | 7/1985 | Junot et al. | 123/489 |
| 4,676,213 | 6/1987 | Itsuji et al. | 123/489 X |
| 4,759,332 | 7/1988 | Morozumi | 123/489 |
| 4,777,922 | 10/1988 | Mieno et al | 123/489 X |
| 4,896,643 | 1/1990 | Blümel | 123/489 |
| 4,915,081 | 4/1990 | Fujimoto et al. | 123/489 |
| 4,932,383 | 6/1990 | Zechnall et al. | 123/489 |
| 4,938,196 | 7/1990 | Hoshi et al. | 123/489 |

Primary Examiner—Willis R. Wolfe
Attorney, Agent, or Firm—Arthur L. Lessler

[57] ABSTRACT

An improved method of determining activation of an exhaust gas concentration sensor for detecting the concentration of an exhaust gas ingredient in exhaust gases from an internal combustion engine. The sensor comprises an exhaust gas ingredient-detecting element, and a heater for heating the element. An output signal from the sensor is used for air-fuel ratio feedback control of an air-fuel mixture supplied to the engine. It is determined that activation of the sensor has been completed when an output voltage from the sensor has become lower than a predetermined activation-determining reference voltage. The predetermined activation-determining reference voltage is changed depending on a time period over which the heater has been energized while the engine is in an operating condition under which the air-fuel ratio feedback control should be carried out.

4 Claims, 5 Drawing Sheets

METHOD OF DETERMINING ACTIVATION OF AN EXHAUST GAS CONCENTRATION SENSOR EQUIPPED WITH A HEATER

BACKGROUND OF THE INVENTION

This invention relates to a method of determining activation of an exhaust gas concentration sensor, and more particularly to a method of determining activation of an exhaust gas concentration sensor having an exhaust gas concentration-detecting element and a heater for heating the element.

In general, an oxygen concentration sensor (hereinafter referred to as "the $O_2$ sensor") is used as an exhaust gas concentration sensor for use in the air-fuel ratio feedback control of an internal combustion engine. The $O_2$ sensor cannot accurately detect the concentration of oxygen unless it is used in a sufficiently activated state. Therefore, it is necessary to determine whether or no activation of the $O_2$ sensor has been completed, and it is well known to determine that the $O_2$ sensor has been activated when the output voltage of the $O_2$ sensor becomes lower than a predetermined reference value (e.g. 0.4 V).

However, according to this method, in some cases, e.g. in a case where the engine is restarted after completion of warming-up of the engine, the $O_2$ sensor is erroneously determined to be inactive although it has actually been activated. Therefore, there has been proposed, by U.S. Pat. No. 4,759,332, another method of determining activation of the $O_2$ sensor in which the predetermined reference value is set to a higher value before a predetermined time period elapses than after the predetermined time period has elapsed.

In the meanwhile, it is conventionally known to provide a heater for the $O_2$ sensor in order to reduce the time required for activation of the $O_2$ sensor when the weather is cold or on like occasions.

In the case of the $O_2$ sensor equipped with the heater, activation thereof is usually completed if the heater has been energized over a predetermined time period while it is operating normally, irrespective of the warmed-up condition of the engine, the ambient temperature, etc. However, there is a case where the air-fuel ratio is enriched due to fuel attached to inner wall surfaces of the intake pipe, so that the output voltage of the $O_2$ sensor continues to assume a high value (e.g. approximately 1.0 V) even when the sensor has actually been activated. In such a case, the $O_2$ sensor is determined to be inactive, and hence the start of the air-fuel ratio feedback control is delayed, which adversely affects purification of exhaust gases.

SUMMARY OF THE INVENTION

It is the object of the invention to provide a method of determining activation of an $O_2$ sensor equipped with a heater, which is capable of preventing delay of determination of activation of the $O_2$ sensor due to causes other than failure of the $O_2$ sensor, and hence starting the air-fuel ratio feedback control earlier.

To attain the above object, the invention provides a method of determining activation of an exhaust gas concentration sensor for detecting the concentration of an exhaust gas ingredient in exhaust gases from an internal combustion engine, the sensor comprising an exhaust gas ingredient-detecting element, and a heater for heating the element, air-fuel ratio feedback control of an air-fuel mixture supplied to the engine being carried out in response to an output signal from the sensor, the method including the step of determining that activation of the sensor has been completed when an output voltage from the sensor has become lower than a predetermined activation-determining reference voltage.

The method according to the present invention is characterized by comprising the steps of:

(1) determining whether or not the engine is in an operating condition under which the air-fuel ratio feedback control should be carried out; and (2) changing the predetermined activation-determining reference voltage depending on a time period over which the heater has been energized while the engine is in the operating condition.

Preferably, the method includes the step of detecting a temperature of the engine, and the changing of the predetermined activation-determining reference voltage is inhibited when the detected temperature of the engine is equal to or lower than a first predetermined value.

More preferably, the changing of the predetermined activation-determining reference voltage is inhibited when the sensor has become inactive again after activation of the sensor was once completed.

Preferably, the method includes the steps of detecting a temperature of the engine, detecting the rotational speed of the engine, and detecting the speed of a vehicle in which the engine is installed, and when a state in which the detected temperature of the engine is higher than a second predetermined value, the detected rotational speed of the engine is higher than a predetermined value, the detected speed of the vehicle is lower than a predetermined value, and the engine is in the operating condition under which the air-fuel ratio feedback control should be carried out, has continued over a predetermined time period, it is determined that activation of the sensor has been completed irrespective of the output voltage from the sensor.

The above and other objects, features, and advantages of the invention will become more apparent from the ensuing detailed description taken in conjunction with the accompanying drawings.

DETAILED DESCRIPTION

The invention will now be described in detail with reference to the drawings showing an embodiment thereof.

Figure 1:
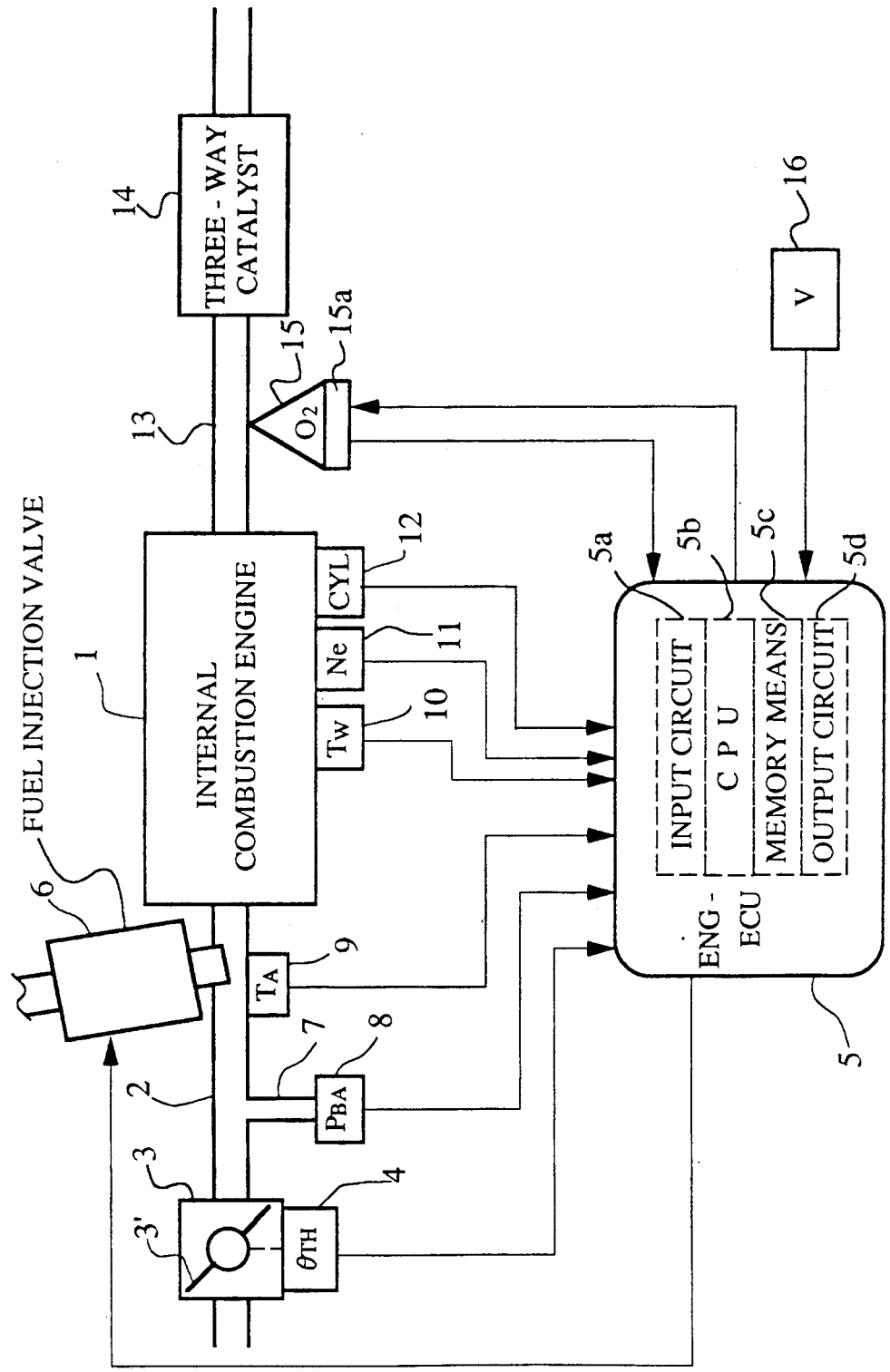
FIG. 1 is a block diagram illustrating the whole arrangement of a fuel supply control system for an internal combustion engine for carrying out the method of the invention.

Referring first to FIG. 1, there is shown the whole arrangement of a fuel supply control system for an internal combustion engine, which is adapted to carry out the method according to the invention. In the figure, reference numeral 1 designates an internal combustion engine for automotive vehicles. Connected to the cylinder block of the engine 1 is an intake pipe 2 across which is arranged a throttle body 3 accommodating a throttle valve 3' therein. A throttle valve opening ($\theta_{TH}$) sensor 4 is connected to the throttle valve 3' for generating an electric signal indicative of the sensed throttle valve opening and supplying same to an electronic control unit (hereinafter called "the ECU") 5.

Fuel injection valves 6, only one of which is shown, are inserted into the interior of the intake pipe at locations intermediate between the cylinder block of the engine 1 and the throttle valve 3' and slightly upstream of respective intake valves, not shown. The fuel injection valves 6 are connected to a fuel pump, not shown, and electrically connected to the ECU 5 to have their valve opening periods controlled by signals therefrom.

On the other hand, an intake pipe absolute pressure ($P_{BA}$) sensor 8 is provided in communication with the interior of the intake pipe 2 at a location immediately downstream of the throttle valve 3' for supplying an electric signal indicative of the sensed absolute pressure within the intake pipe 2 to the ECU 5. An intake air temperature ($T_A$) sensor 9 is inserted into the intake pipe 2 at a location downstream of the intake pipe absolute pressure sensor 8 for supplying an electric signal indicative of the sensed intake air temperature $T_A$ to the ECU 5.

An engine coolant temperature ($T_W$) sensor 10, which may be formed of a thermistor or the like, is mounted in the cylinder block of the engine 1, for supplying an electric signal indicative of the sensed engine coolant temperature $T_W$ to the ECU 5. An engine rotational speed (Ne) sensor 11 and a cylinder-discriminating (CYL) sensor 12 are arranged in facing relation to a camshaft or a crankshaft of the engine 1, neither of which is shown. The engine rotational speed sensor 11 generates a pulse as a TDC signal pulse at each of predetermined crank angles whenever the crankshaft rotates through 180 degrees, while the cylinder-discriminating sensor 12 generates a pulse at a predetermined crank angle of a particular cylinder of the engine, both of the pulses being supplied to the ECU 5.

A three-way catalyst 14 is arranged within an exhaust pipe 13 connected to the cylinder block of the engine 1 for purifying noxious components such as HC, CO, and NOx. An $O_2$ sensor 15 as an exhaust gas concentration sensor is mounted in the exhaust pipe 13 at a location upstream of the three-way catalyst 14, for sensing the concentration of oxygen present in exhaust gases emitted from the engine 1 and supplying an electric signal indicative of the sensed oxygen concentration to the ECU 5. The $O_2$ sensor has a detecting element for detecting the concentration of oxygen, and a heater 15a for heating the detecting element. Turning-on or -off of the heater 15a is controlled by the ECU 5. Further, a vehicle speed sensor 16 is connected to the ECU 5 for detecting the vehicle speed V and supplying a signal indicative of the detected vehicle speed V to the ECU 5.

The ECU 5 comprises an input circuit 5a having the functions of shaping the waveforms of input signals from various sensors, shifting the voltage levels of sensor output signals to a predetermined level, converting analog signals from analog-output sensors to digital signals, and so forth, a central processing unit (hereinafter called "the CPU") 5b, memory means 5c storing various operational programs which are executed in the CPU 5b and for storing results of calculations therefrom, etc., and an output circuit 5d which outputs driving signals to the fuel injection valves 6.

The CPU 5b operates in response to the abovementioned signals from the sensors to determine operating conditions in which the engine 1 is operating, such as an air-fuel ratio feedback control region in which the fuel supply is controlled in response to the detected oxygen concentration in the exhaust gases, and open-loop control regions, and calculates, based upon the determined operating conditions, the valve opening period or fuel injection period $T_{OUT}$ over which the fuel injection valves 6 are to be opened, by the use of the following equation in synchronism with inputting of TDC signal pulses to the ECU 5.

$$T_{OUT} = T_i \times K_1 \times K_{O2} + K_2 \ldots (1)$$

where $T_i$ represents a basic value of the fuel injection period $T_{OUT}$ of the fuel injection valves 6, which is read from a Ti map set in accordance with the engine rotational speed Ne and the intake pipe absolute pressure $P_{BA}$.

$K_{O2}$ is an air-fuel ratio feedback control correction coefficient whose value is determined in response to the oxygen concentration in the exhaust gases, i.e. the output voltage $V_{O2}$ of the $O_2$ sensor 15, during feedback control, while it is set to respective predetermined appropriate values while the engine is in predetermined operating regions (the open-loop control regions) other than the feedback control region.

$K_1$ and $K_2$ are other correction coefficients and correction variables, respectively, which are calculated based on various engine parameter signals to such values as to optimize characteristics of the engine such as fuel consumption and accelerability depending on the operating conditions of the engine.

The CPU 5b supplies through the output circuit 5d, the fuel injection valves 6 with driving signals corresponding to the calculated fuel injection period $T_{OUT}$ determined as above, over which the fuel injection valves 6 are opened, and the heater 15a of the $O_2$ sensor 15 with signals for controlling turning-on or -off of the heater 15a.

Figure 2A:
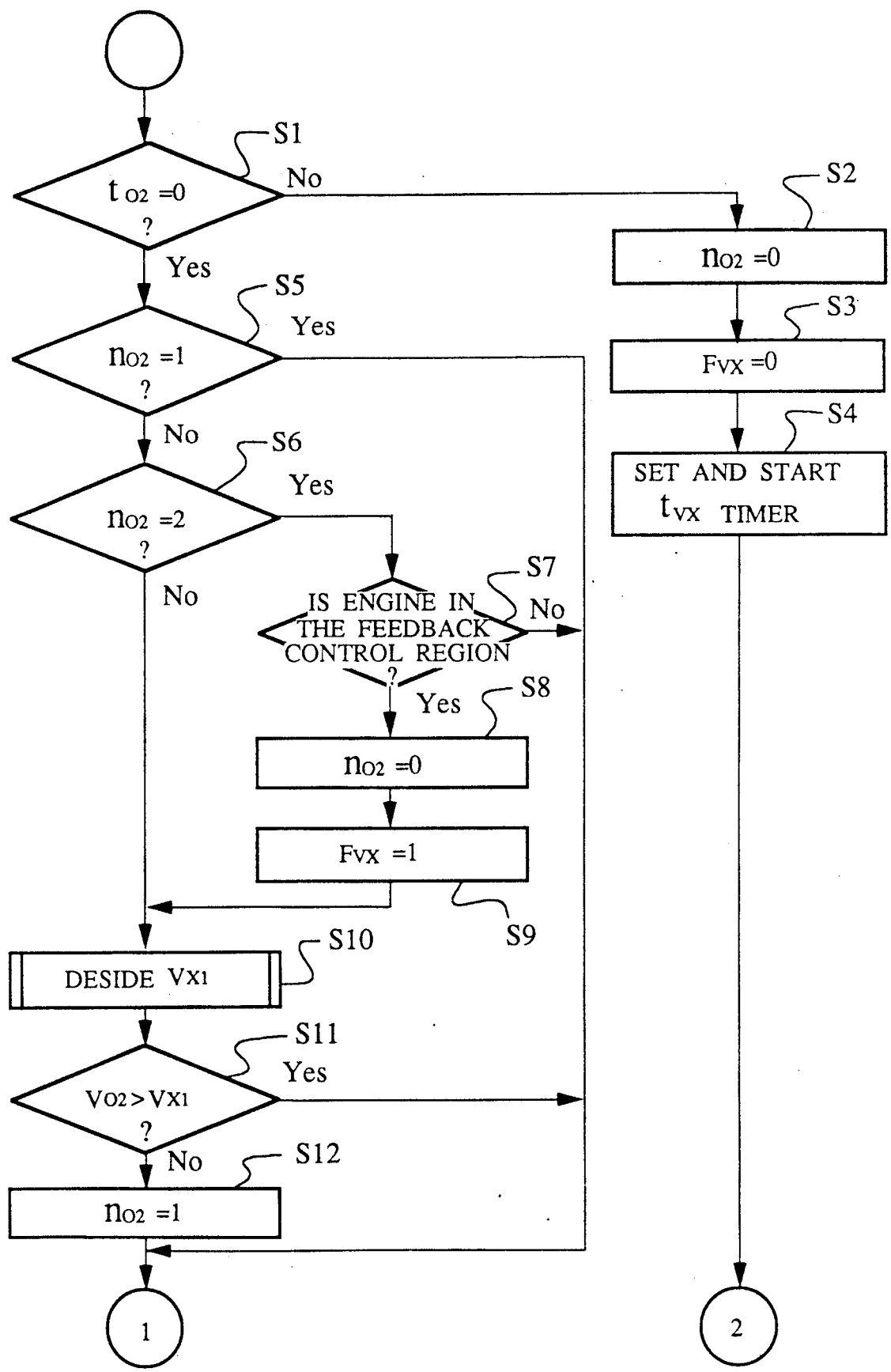
FIG. 2 is a flowchart of a program for carrying out determination of activation of an exhaust gas concentration sensor appearing in FIG. 1.
Figure 2B:
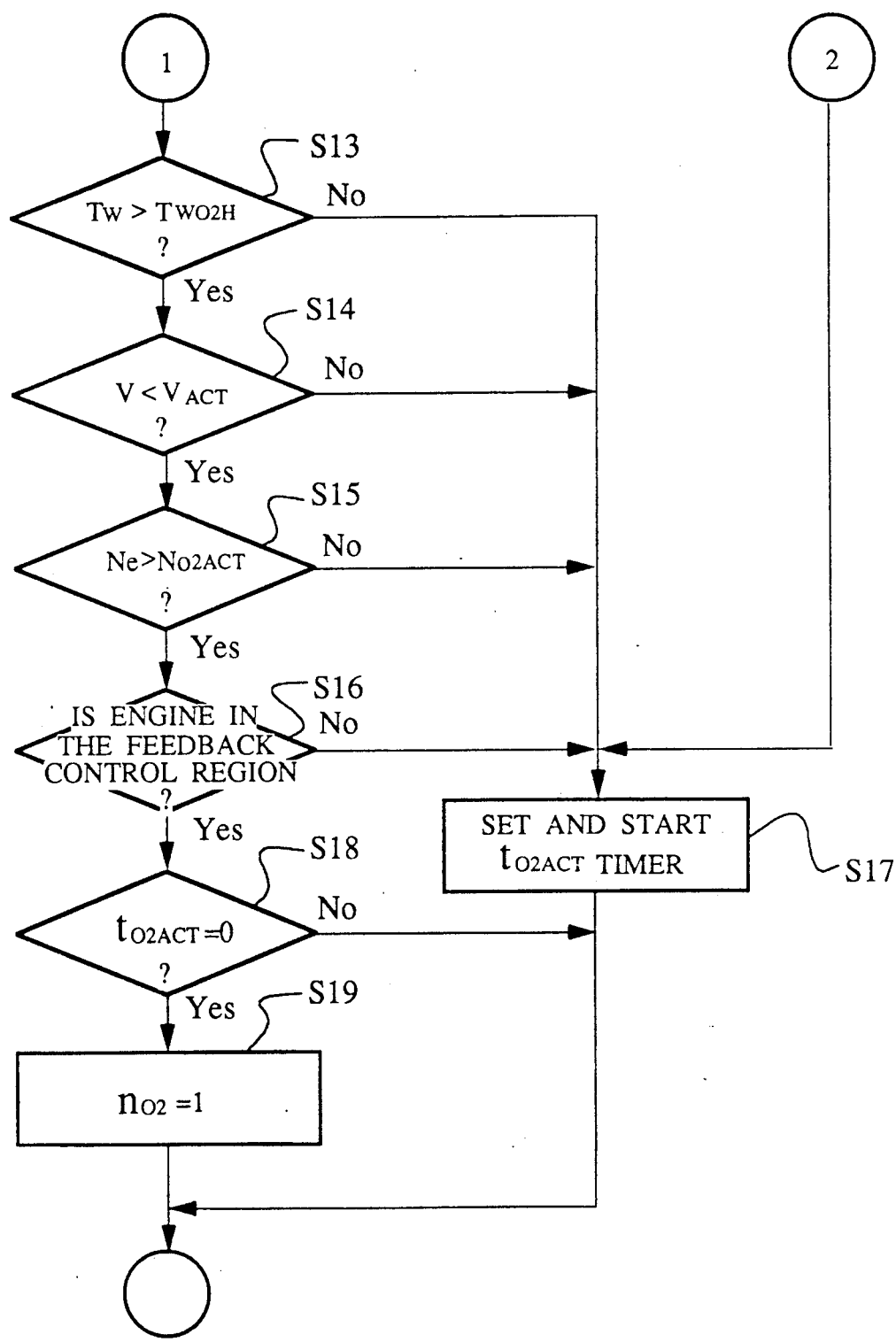

FIG. 2 shows a program for carrying out determination of activation of the $O_2$ sensor 15. At a step S1, it is determined whether or not the count value of a $t_{O2}$ timer, which is provided for counting a predetermined time period $t_{O2}$ after the ignition switch is turned on, is equal to 0. If the answer to this question is negative (No), i.e. if the predetermined time period $t_{O2}$ has not elapsed after the ignition switch was turned on, a flag $\eta_{O2}$ for indicating an active or inactive state of the $O_2$ sensor 15 is set to 0 at a step S2. The flag $\eta_{O2}$ indicates an inactive state thereof when it is set to 0, whereas it indicates an activated state thereof when it is set to 0. In the former case, active state detection is carried out, whereas in the latter case, inactive state detection is carried out (the inactive state detection is carried out by a subroutine, not shown). Further, if the flag $\eta_{O2}$ is set to 2, it indicates an inactive state of the $O_2$ sensor in the case where the $O_2$ sensor 15 has become inactive after it was once activated. In this case, active state detection is not carried out.

Then at a step S3, a flag $F_{VX}$ is set to 0. At a step S4, a $t_{VX}$ timer is set to a predetermined time period $t_{VX}$ (e.g. 1 minute) and started, and further at a step S17, a $t_{O2ACT}$ timer is set to a predetermined time period $t_{O2ACT}$ (e.g. 5 minutes) and started, followed by terminating the present program. The flag $F_{VX}$ is set to 1 when the flag $\eta_{O2}$ is equal to 2 and at the same time the operating condition of the engine is in the feedback control region. The $t_{VX}$ timer is used for counting the duration of a first predetermined operating condition of the engine in a subroutine shown in FIG. 3 and referred to hereinafter. The $t_{O2ACT}$ timer is used for counting the duration of a second predetermined operating condition of the engine referred to hereinafter.

Thus, before the predetermined time period $t_{O2}$ elapses after the ignition switch gas turned on, the $O_2$ sensor is determined to be inactive ($\eta_{O2}=0$) irrespective of the output voltage $V_{O2}$ of the $O_2$ sensor.

If the answer to the question of the step S1 is affirmative (Yes), i.e. if the predetermined time period $t_{O2}$ has elapsed after the ignition switch was turned on, it is determined at a step S5 whether or not the flag $\eta_{O2}$ is equal to 1. If the answer to this question is affirmative (Yes), i.e. if $\eta_{O2}=1$, which means that activation of the $O_2$ sensor has been completed, the program proceeds to a step S13, whereas if the answer is negative (No), i.e. if $\eta_{O2}=0$ or 2, it is further determined at a step S6 whether or not the flag $\eta_{O2}$ is equal to 2. If the answer to the question of the step S6 is negative (No), i.e. if $\eta_{O2}=0$, the program jumps to a step S10, whereas the answer is affirmative (yes), i.e. if $\eta_{O2}=2$, it is determined at a step S7 whether or not the operating condition of the engine is in the air-fuel ratio feedback control region. This determination is carried out based on the engine rotational speed Ne, the fuel injection period $T_{OUT}$ calculated based on the above-described equation (1), etc. If the answer to the question of the step S7 is negative (No), the program jumps to a step S13, whereas if the answer is affirmative (Yes), the flag $\eta_{O2}$ is set to 0 at a step B8 and the flag $F_{VX}$ is set to 1 at a step S9, followed by the program proceeding to the step S10.

Figure 3:
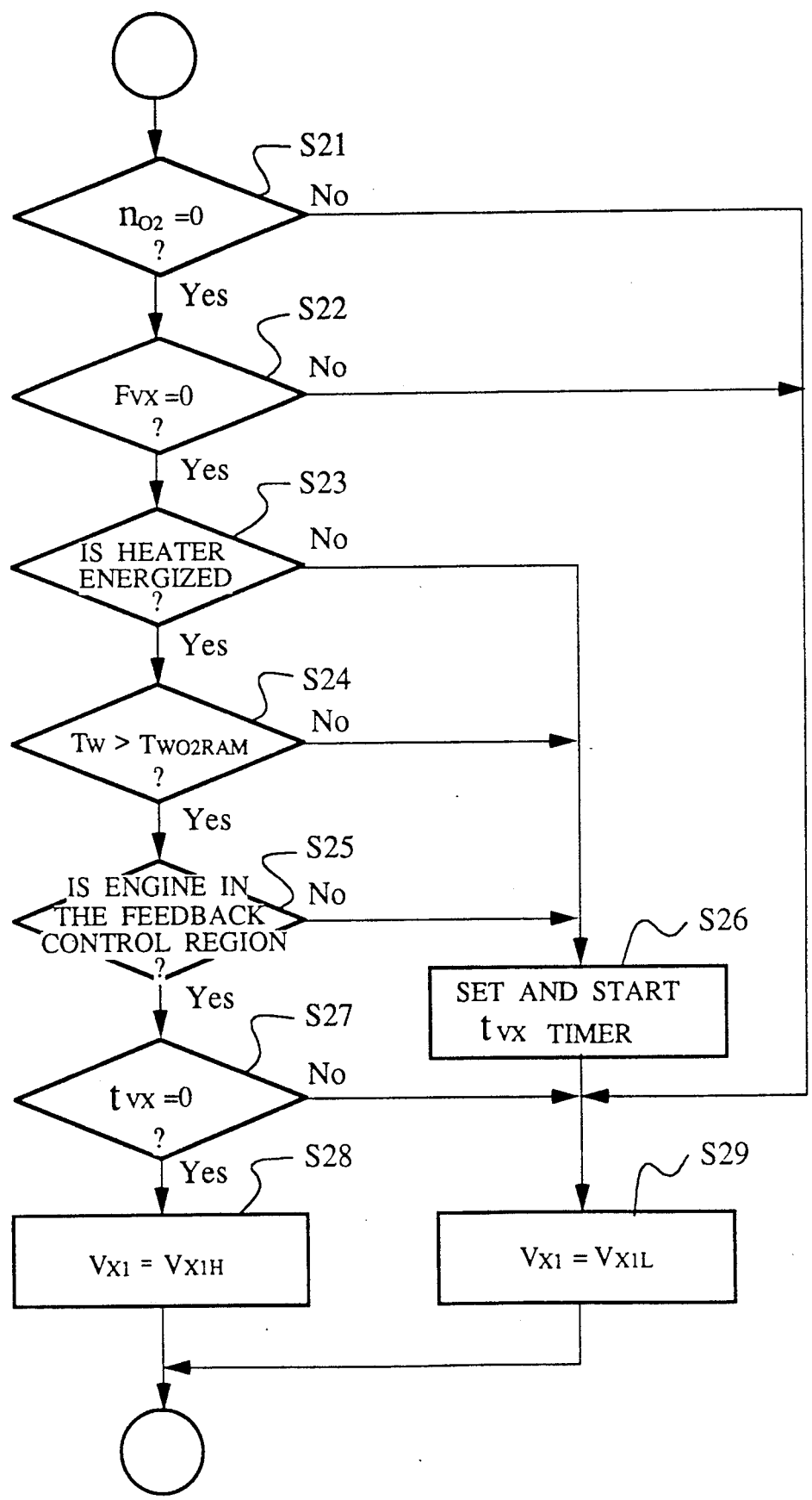
FIG. 3 is a flowchart of a subroutine for setting an activation-determining reference voltage ($V_{X1}$)

At the step S10, there is carried out a $V_{X1}$ subroutine of FIG. 3 for deciding an activation-determining reference voltage $V_{X1}$. First, at a step S21 in the flowchart of FIG. 3, it is determined whether or not the flag $\eta_{O2}$ is equal to 0. If the answer to this question is negative (No), i.e. if $N\eta_{O2} = 1$ or 2, the reference voltage $V_{X1}$ is set to a first predetermined value $V_{X1L}$ (e.g. 0.4 V) at a step S29, followed by terminating the present subroutine.

If the answer to the question of the step S21 is affirmative (Yes), i.e. if $\eta_{O2}=0$, it is determined at a step S22 whether or not the flag $F_{VX}$ is equal to 0. If the answer to this question is negative (No), the program proceeds to the step S29, whereas if the answer is affirmative (Yes), it is determined at a step S23 whether or not the heater 15a of the $O_2$ sensor 15 is energized. If the answer to this question is affirmative (Yes), i.e. if the heater 15a is energized, it is determined at a step S24 whether or not the engine coolant temperature $T_W$ is higher than a predetermined value $T_{WO2RAM}$ (e.g 25° C). If the answer to this question is affirmative (Yes), i.e. if $T_W>T_{WO2RAM}$, it is determined at a step S25 whether or not the operating condition of the engine is in the air-fuel ratio feedback control region.

If any of the answers to the questions of the steps S23 to S25 is negative (No), i.e. if the heater 15a is not energized, or if $T_W \leq T_{WO2RAM}$, or if the engine is not in the air-fuel ratio feedback control region, the $t_{VX}$ timer is set to the predetermined time period $t_{VX}$ and started at a step S26, and then the program proceeds to the step S29.

If all the answers to the questions of the steps S23 to S25 are affirmative (Yes), i.e. if the heater 15a is energized, $T_W>T_{WO2RAM}$, and the engine is in the air-fuel ratio feedback control region (=the first predetermined operating condition), it is determined at a step S27 whether or not the count value of the $t_{VX}$ timer started at the step S26 (or at the step S4 in FIG. 2) is equal to 0. If the answer is negative (No), i.e. if the first predetermined operating condition has not continued over the predetermined time period $t_{VX}$, the program proceeds to the step S29, whereas if the answer is affirmative (Yes), i.e. after the first predetermined operating condition has continued over the predetermined time period $t_{VX}$, the reference voltage $V_{X1}$ is set to a second predetermined value $V_{X1H}$ (e.g. 1.0 V) higher than the first predetermined value $V_{X1L}$ at a step S28, followed by terminating the present subroutine.

According to the above-described $V_{X1}$ subroutine, only when the first predetermined operating condition has continued for the predetermined time period $t_{VX}$ or longer, the reference voltage $V_{X1}$ is set to the second predetermined value $V_{X1H}$, and in the other cases, it is set to the first predetermined value $V_{X1L}$.

Referring again to FIG. 2, it is determined at a step S11 whether or not the output voltage $V_{O2}$ of the $O_2$ sensor 15 is higher than the reference voltage $V_{X1}$. If the answer to this question is affirmative (Yes), i.e. if $V_{O2}>V_{X1}$, the program proceeds to the step S13, whereas if the answer is negative (No), i.e. if $V_{O2} \leq V_{X1}$, it is judged that activation of the $O_2$ sensor has been completed and the flag $\eta_{O2}$ is set to 1 at a step S12, followed by the program proceeding to the step S13.

At the step S13, it is determined whether or not the engine coolant temperature is higher than a predetermined value $T_{WO2H}$ (e.g. 25° C.). If the answer to this question is affirmative (Yes), it is determined at a step S14 whether or not the vehicle speed V is lower than a predetermined value $V_{ACT}$ (e.g 15 km/h). If the answer to this question is affirmative (Yes), it is determined at a step S15 whether or not the engine rotational speed Ne is higher than a predetermined value $N_{O2ACT}$ (e.g 2,000 rpm). If the answer to this question is affirmative (Yes), it is determined at a step S16 whether or not the engine is in the air-fuel ratio feedback control region.

If any of the answers to the questions of the steps S13 to S16 is negative (No), the program proceeds to a step S17, whereas if all the answers to the questions of the steps S13 to S16 are affirmative (Yes), i.e. if $T_W>T_{WO2H}$, $V<V_{ACT}$, $Ne>N_{O2ACT}$, and the engine is in the air-fuel ratio feedback control region (=the second predetermined operating condition), it is determined at a step S18 whether or not the count value of the $t_{O2ACT}$ timer is equal to 0. If the answer to this question is negative (No), the present program is immediately terminated, whereas if the answer is affirmative (Yes), it is judged that activation of the $O_2$ sensor 15 has been completed and the flag $\eta_{O2}$ is set to 1 at a step S19, followed by terminating the present program.

Figure 4A:
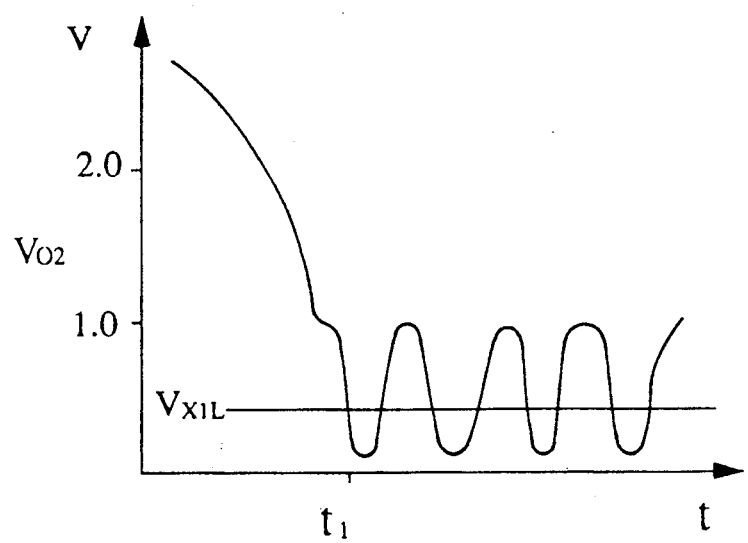
FIGS. 4a and 4b are diagrams showing changes in the output voltage ($V_{O2}$) of the exhaust gas concentration sensor with the lapse of time.
Figure 4B:
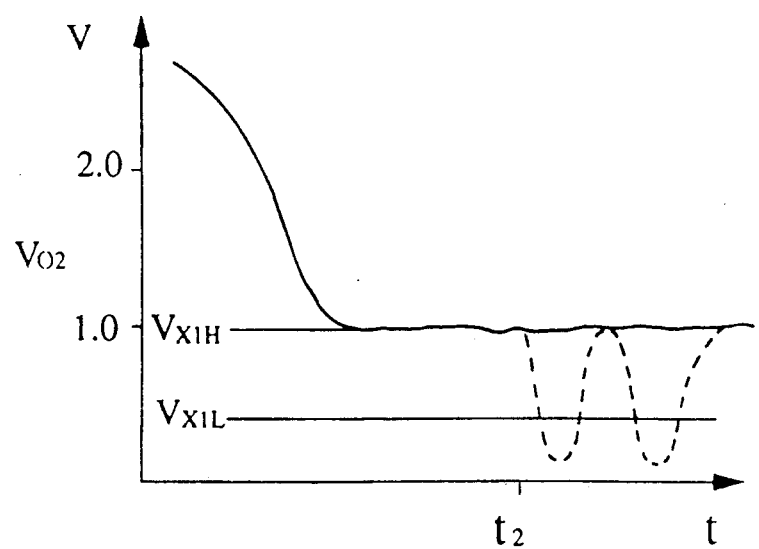

According to the activation-determining method shown in FIG. 2, normally, the output voltage $V_{O2}$ becomes lower as time elapses, and the $O_2$ sensor is determined to be activated at a time point $t_1$ in FIG. 4a, so that thereafter the air-fuel ratio feedback control is carried out, as shown in FIG. 4a. On the other hand, in the case where the air-fuel ratio is enriched due to fuel attached to inner wall surfaces of the intake pipe etc., the output voltage $V_{O2}$ remains at or around 1.0 V, as shown in FIG. 4b. However, at a time point $t_2$ at which the first predetermined operating condition (the heater 15a is energized, the engine coolant temperature $T_W >$ $T_{HO2RAM}$, and the engine is in the air-fuel ratio feedback control region) has continued for the predetermined time period $t_{VX}$, the reference voltage $V_{X1}$ is changed from the first predetermined value $V_{X1L}$ to the second predetermined value $V_{X1H}$. As a result, the $O_2$ sensor is determined to be activated approximately at the time point $t_2$, so that thereafter the air-fuel ratio feedback control is carried out (as shown by the broken line of FIG. 4b). Thus, it is possible to prevent the output voltage $V_{O2}$ from remaining around 1.0 V to delay the start of the air-fuel ratio feedback control (as shown by the solid line of FIG. 4b).

As is clear from the above detailed description, according to the method of the present invention, since the activation-determining reference voltage is changed depending on a time period over which the engine has been in the air-fuel ratio feedback control region and at the same time the heater has been energized, it is possible to properly determine activation of the exhaust gas concentration sensor even if the air-fuel ratio is enriched due to fuel attached to inner wall surfaces of the intake pipe etc. Accordingly, it is possible to prevent delay of determination of activation of the exhaust gas concentration sensor due to causes other than failure of the sensor, and hence start the air-fuel ratio feedback control earlier.

What is claimed is:

1. In a method of determining activation of an exhaust gas concentration sensor for detecting the concentration of an exhaust gas ingredient in exhaust gases from an internal combustion engine, said sensor comprising an exhaust gas ingredient-detecting element, and a heater for heating said element, air-fuel ratio feedback control of an air-fuel mixture supplied to said engine being carried out in response to an output signal from said sensor, said method including the step of determining that activation of said sensor has been completed when an output voltage from said sensor has become lower than a predetermined activation-determining reference voltage, the improvement comprising the steps of:
(1) determining whether or not said engine is in an operating condition under which said air-fuel ratio feedback control should be carried out; and
(2) changing said predetermined activation-determining reference voltage depending on a time period over which said heater has been energized while said engine is in said operating condition.

2. A method according to claim 1, including the step of detecting a temperature of said engine, and wherein said changing of said predetermined activation-determining reference voltage is inhibited when the detected temperature of said engine is equal to or lower than a first predetermined value.

3. A method according to claim 1 or 2, wherein said changing of said predetermined activation-determining reference voltage is inhibited when said sensor has become inactive again after activation of said sensor was once completed.

4. A method according to claim 1 or 2, including the steps of detecting a temperature of said engine, detecting the rotational speed of said engine, and detecting the speed of a vehicle in which said engine is installed, and wherein when a state in which the detected temperature of said engine is higher than a second predetermined value, the detected rotational speed of said engine is higher than a predetermined value, the detected speed of said vehicle is lower than a predetermined value, and said engine is in said operating condition under which said air-fuel ratio feedback control should be carried out, has continued over a predetermined time period, it is determined that activation of said sensor has been completed irrespective of said output voltage from said sensor.

* * * * *